(12) United States Patent
Wu et al.

(10) Patent No.: US 8,367,404 B2
(45) Date of Patent: Feb. 5, 2013

(54) CHIMERAL INTERNAL RIBOSOMAL ENTRY SITE SEQUENCE AND USES THEREOF

(75) Inventors: Tzong-Yuan Wu, Panchiao (TW); Ming-Kun Liu, Lugang Township (TW)

(73) Assignee: Chung Yuan Christian University, Jhongli, Taoyuan County (TW)

( * ) Notice: Subject to any disclaimer, the term of this patent is extended or adjusted under 35 U.S.C. 154(b) by 16 days.

(21) Appl. No.: 13/046,744

(22) Filed: Mar. 13, 2011

(65) Prior Publication Data

US 2012/0231536 A1 Sep. 13, 2012

(51) Int. Cl.
C12N 15/00 (2006.01)
C07H 21/04 (2006.01)
C12N 5/00 (2006.01)
(52) U.S. Cl. .................... 435/320.1; 536/23.5
(58) Field of Classification Search .............. None
See application file for complete search history.

(56) References Cited

PUBLICATIONS

Ying-Ju Chen, Wein-Shue Chen, Tzong-Yuan Wu; Title: Development of a bi-cistronic baculovirus expression vector by the Rhopalosiphum padi virus 50 internal ribosome entry site; Sep. 23, 2005, p. 616-623, V01.335, No. 2, Publisher: Biochemical and Biophysical Research Communications.*
Yi-Jane Wu, Chao-Yi Teng, Yu-Jie Chen, Seng-Chi Chen, Ying-Ju Chen, Yi-Ting Lin, Tzong-Yuan Wu; Title: Internal ribosome entry site of Rhopalosiphum padi virus is functional in mammalian cells and has cryptic promoter activity in baculovirus-infected Sf21 cells; Journal, Aug. 4, 2008, p. 965-974, vol. 29: Issue 8, Publisher: Acta Pharmacologica S.*
Ying-Ju Chen, Wein-Shue Chen, Tzong-Yuan Wu; Title: Development of a bi-cistronic baculovirus expression vector by the Rhopalosiphum padi virus 50 internal ribosome entry site; Sep. 23, 2005, p. 616-623, vol. 335, No. 2, Publisher: Biochemical and Biophysical Research Communications.
Yi-Jane Wu, Chao-Yi Teng, Yu-Jie Chen, Seng-Chi Chen, Ying-Ju Chen, Yi-Ting Lin, Tzong-Yuan Wu; Title: Internal ribosome entry site of Rhopalosiphum padi virus is functional in mammalian cells and has cryptic promoter activity in baculovirus-infected Sf21 cells; Journal, Aug. 4, 2008, p. 965-974, vol. 29: Issue 8, Publisher: Acta Pharmacologica Sinica, Published online.

* cited by examiner

*Primary Examiner* — Nancy T Vogel
*Assistant Examiner* — Catherine Hibbert
(74) *Attorney, Agent, or Firm* — Chih Feng Yeh; Huntington IP Consulting Co., Ltd.

(57) ABSTRACT

An improved baculovirus vector capable of expressing genes in mammalian or insect host cells, and the uses thereof are disclosed. The improved baculovirus vector includes in sequence: a promoter; a first nucleic acid operably linked to the promoter for expressing a first protein in the mammalian or insect host cells; a chimera internal ribosomal entry site (IRES) comprising a portion of an enterovirus (EV) IRES sequence at least 90% identical to SEQ ID NO: 1 and a portion of a *Rhopalosiphum padi* virus (RhPV) IRES sequence at least 90% identical to SEQ ID NO: 2; and a second nucleic acid operable linked to the portion of the RhPV IRES sequence for expressing a second protein in the mammalian or insect host cells.

5 Claims, 17 Drawing Sheets
(17 of 17 Drawing Sheet(s) Filed in Color)

(A) vCMV-DRhirE (B) vCMV-DRhir290E (C) vCMV-DRhir291E (D) vCMV-DRhir309E (E) vCMV-DRhir411E (F) vCMV-DRhir423E (A)  pCMV-DRhirE (B)  pCMV-DRhir290E (C) pCMV-DRhir291E (D) pCMV-DRhir309E (E) pCMV-DRhir411E (F) pCMV-DRhir423E

FIG 6

(A) vCMV-DRhir309E  (B) vCMV-DRhir309E (TAAG△)

(C) vCMV-DRhir309E (T328A)  (D) vCMV-DRhir309E (T332A)

(A) pCMV-DRhir309E (B) pCMV-DRhir309E (TAAG Δ)

(C) pCMV-DRhir309E (T328A)

(D) pCMV-DRhir309E (T332A)

FIG 11

(A) vCMV-DRhirE (B) vCMV-DRhir309E (C) vCMV-DEV71E (D) vCMV-DEV71 (3'Δ100) ·
RP110E

FIG 12

EGFP intensity (RFU/μg)

- vCMV-DRhirE: 100%
- vCMV-DRhir309E: 60%
- vCMV-DEV71E: 2%
- vCMV-DEV71(3'Δ100)Rhir309E: 105%

(A) pCMV-DRhirE (B) pCMV-DRhir309E

FIG 13

(C) pCMV-DEV71E (D) pCMV-DEV71 3'△100 - Rhir309E

SEQUENCE LISTING

<160> NUMBER OF SEQ ID NOS: 2

<210> SEQ ID NO 1
<211> LENGTH: 645
<212> TYPE: DNA

```
<213> ORGANISM: enterovirus

<400> SEQUENCE: 1
ttaaaacagc ctgtgggttg cacccaccca cagggcccac tgggcgctag cactctggta      60
ctgaggtacc tttgtgcgcc tgtttttact cccttcccc cgaagtaact tagaagctgt     120
aaatcaacga tcaatagcag gtgtggcaca ccagtcatac cttgatcaag cacttctgtt    180
tccccggact gagtatcaat aggctgctcg cgcggctgaa ggagaaaacg ttcgttaccc    240
gaccaactac ttcgagaagc ttagtaccac catgaacgag gcagggtgtt tcgctcagca    300 caacccagt gtagatcagg ctgatgagtc actgcaaccc ccatgggcga ccatggcagt    360
ggctgcgttg gcggcctgcc catggagaaa tccatgggac gctctaattc tgacatggtg    420
tgaagagcct attgagctag ctggtagtcc tccggcccct gaatgcggct aatcctaact    480
gcggagcaca tgctcacaaa ccagtgggtg gtgtgtcgta acgggcaact ctgcagcgga    540
accgactact ttgggtgtcc gtgtttcctt ttattcctat attggctgct tatggtgaca    600
atcaaagagt tgttaccata tagctattgg attggccatc cggtg                    645

<210> SEQ ID NO 2
<211> LENGTH: 110
<212> TYPE: DNA
<213> ORGANISM: Rhopalosiphum padi virus

<400> SEQUENCE: 2
agttaaagct ttataactat aagtaagccg tgccgaaacg ttaatcggtc gctagttgcg     60
taacaactgt tagtttaatt ttccaaaatt tatttttcac aattttagt                110
```

CHIMERAL INTERNAL RIBOSOMAL ENTRY SITE SEQUENCE AND USES THEREOF

SEQUENCE LISTING

The present disclosure includes a sequence listing incorporated herein by reference on its entirety.

BACKGROUND OF THE INVENTION

1. Field of the Invention

The present disclosure relates, in general, to a chimera internal ribosomal entry site (IRES) sequence and uses thereof. More particularly, the present disclosure is directed to an improved baculovirus vector comprising the chimera IRES sequence for expressing genes in a mammalian or an insect host cell.

2. Description of Related Art

IRES sequences were first discovered in poliovirus RNA and encephalomyocarditis virus RNA, respectively. They are described as distinct regions of RNA molecules that are able to attract the eukaryotic ribosome to the mRNA molecule and, therefore, allow translation initiation to occur. This process is known as the internal initiation of translation.

It is common that IRESes are located at the 5'-untranslated region (5'UTR) of some RNA viruses such as small RNA viruses or hepatitis C viruses and allow translation of the RNAs in a cap-independent manner. When an IRES segment is placed between two reporter open reading frames (ORFs) in an eukaryotic mRNA molecule, it can drive translation of the downstream protein coding region independently of the 5'-cap structure bound to the 5'-end of the mRNA molecule. In such setup, both proteins are produced in the host cell.

In this study, a chimera IRES sequence was produced, and an improved baculovirus vector comprising the chimera IRES sequence for expressing genes in mammalian or insect host cells was disclosed.

SUMMARY

As embodied and broadly described herein, disclosure herein features a chimera internal ribosomal entry site (IRES) sequence and uses thereof.

In one aspect, the present disclosure is directed to a chimera IRES sequence for use in mammalian or insect cells. The chimera IRES sequence includes a portion of an enterovirus (EV) IRES sequence at least 90% identical to SEQ ID NO: 1; and a portion of a *Rhopalosiphum padi* virus (RhPV) IRES sequence at least 90% identical to SEQ ID NO: 2.

According to one preferred embodiment of this disclosure, the portion of RhPV IRES sequence is identical to SEQ ID NO: 2, and possesses an IRES activity in mammalian host cells, and a promoter activity in insect host cells. The IRES activity and the promoter activity of SEQ ID NO: 2 are separate activities and do not interfere with each other.

In another aspect, the present disclosure is directed to an improved baculovirus vector capable of expressing genes in mammalian or insect host cells, and uses thereof.

According to one embodiment of the present disclosure, the baculovirus vector capable of expressing genes in mammalian or insect host cells includes a promoter; a first nucleic acid operably linked to the promoter for expressing a first protein in the mammalian or insect host cells; a chimera IRES sequence comprising a portion of an enterovirus (EV) IRES sequence at least 90% identical to SEQ ID NO: 1, and a portion of a *Rhopalosiphum padi* virus (RhPV) IRES sequence at least 90% identical to SEQ ID NO: 2; and a second nucleic acid operably linked to the chimera IRES sequence for expressing a second protein in the mammalian or insect host cells.

According to one embodiment of the present disclosure, the promoter is a cytomegalovirus (CMV) promoter or a CAG promoter composed of chicken β-actin promoter and CMV enhancer.

According to another embodiment of the present disclosure, the chimera IRES sequence is effective in enhancing the downstream protein translation activity for at least 40%.

According to still another embodiment of the present disclosure, the portion of the RhPV IRES sequence has a promoter activity and is effective to express downstream nucleic acid sequence in insect host cells. In one example, the insect host cells are *S. frugiperda* IPBL-Sf21 insect cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, wherein:

FIG. 6 are fluorescent photographs of Sf21 cells taken on day 4 after being transfected with recombinant baculovirus vectors of example 2.1, including (A) vCMV-DRhir309E, (B) vCMV-DRhir309E (TAAGΔ), (C) vCMV-DRhir309E (T328A), and (D) vCMV-DRhir309E (T332A);

FIG. 11 are fluorescent photographs of Sf21 cells taken on day 4 after being transfected with recombinant baculovirus vectors of example 3.1, including (A) vCMV-DRhir309E, (B) vCMV-DRhir309E, (C) vCMV-DEV71E, and (D) vCMV-DEV71 (3'Δ100) Rhir309E;

FIG. 12 is a bar diagram illustrating the quantification result of EGFP expression on day 4 in Sf21 cells of FIG. 11.

DETAILED DESCRIPTION

Figure 1:
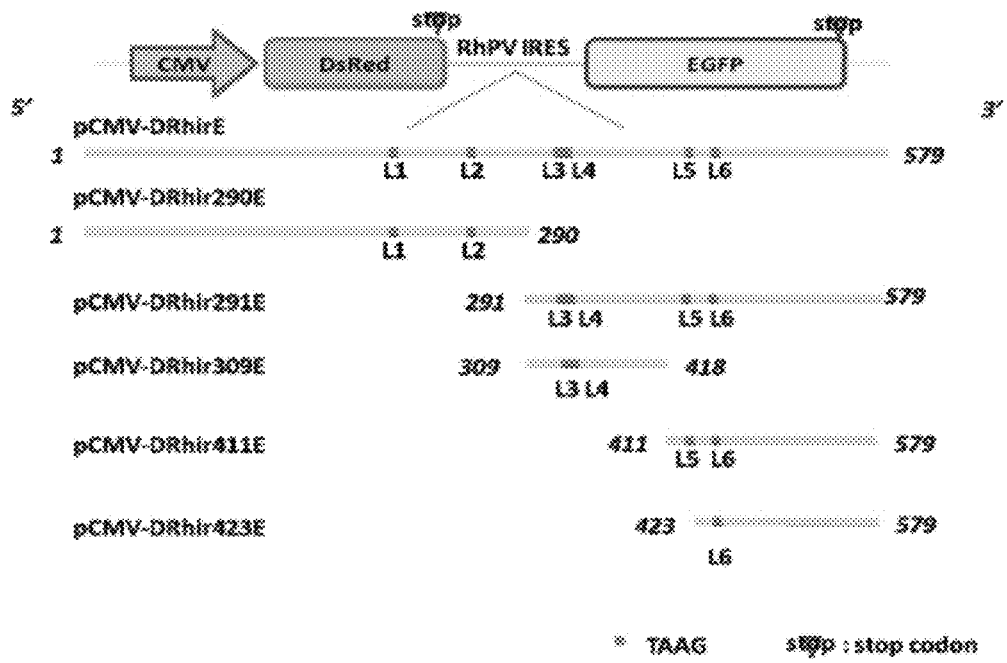
FIG. 1 is a schematic diagram illustrating the construction of recombinant baculovirus plasmids in accordance with one embodiment of this invention.

The detailed description provided below in connection with the appended drawings is intended as a description of the present examples and is not intended to represent the only forms in which the present example may be constructed or utilized. The description sets forth the functions of the examples and the sequence of steps for constructing and operating the examples. However, the same or equivalent functions and sequences may be accomplished by different examples.

The practices of this invention are hereinafter described in detail with respect to a baculovirus vector comprising a chimera IRES sequence for expressing genes in mammalian or insect cells.

According to one aspect of the present disclosure, a chimera IRES sequence is designed and constructed. The chimera IRES sequence comprises from 5' to 3', a portion of an enterovirus (EV) IRES sequence at least 90% identical to SEQ ID NO: 1; and a portion of a *Rhopalosiphum padi* virus (RhPV) IRES sequence at least 90% identical to SEQ ID NO: 2.

The portion of the EV IRES sequence is preferably 90%, 91%, 92%, 93%, 94%, 95%, 96%, 97%, 98%, 99% or 100% identical to SEQ ID NO: 1. In one example, the portion of the EV IRES sequence is 100% identical to SEQ ID NO: 1, which corresponds to the 5' EV 71 IRES sequence from position 1 to 645. According to one embodiment of the present disclosure, the truncated EV 71 IRES sequence or SEQ ID NO: 1 still possesses an IRES activity in mammalian host cells.

The portion of the RhPV IRES sequence is preferably 90%, 91%, 92%, 93%, 94%, 95%, 96%, 97%, 98%, 99% or 100% identical to SEQ ID NO: 2. In one example, the portion of the RhPV IRES sequence is 100% identical to SEQ ID NO: 2, which corresponds to the 5' RhPV IRES sequence from position 309 to 418. In such case, the portion of the PhPV IRES sequence having SEQ ID NO: 2 comprises two adjacent TAAG motifs, and is termed "RP110" herein. According to one preferred embodiment of the present disclosure, RP110 has an IRES activity in mammalian host cells and a promoter activity in insect host cells. The IRES activity and the promoter activity are separate activities and are independent of each other. According to one preferred embodiment of the present disclosure, the promoter activity of RP110 is not affected by the presence of the truncated EV 71 IRES in the chimera IRES sequence. Suitable insect host cells for use in the present disclosure are *S. frugiperda* IPBL-Sf21 insect cells.

"Nucleotide sequence", "polynucleotide" or "nucleic acid" can be used interchangeably and are understood to mean, according to the present disclosure, either a double-stranded DNA, a single-stranded DNA or products of transcription of the said DNAs (e.g., RNA molecules). It should also be understood that the present disclosure does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

The percentage of identity between a subject sequence and a reference standard can be determined by submitting both sequences to a computer analysis with any parameters affecting the outcome of the alignment set to the default position. Optimal alignment of sequences for aligning a comparison window are well known to those skilled in the art and may be conducted by tools such as the homology alignment algorithm, include, but are not limited to GAP, BESTFIT, FASTA, and TFASTA (Accelrys Inc., Burlington, Mass., USA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more nucleic acid sequences may be to a full-length nucleic acid sequence or a portion thereof, or to a longer nucleic acid sequence. In some instances, a subject sequence and the reference standard can exhibit the required percent identity without the introduction of gaps into one or both sequences. In many instances, the extent of identity will be evident without computer assistance.

According to another aspect of the present disclosure, an improved baculovirus vector for efficient gene expression in a mammalian or insect host cell system is provided. The improved baculovirus vector is characterized in having the chimera IRES sequence as described above. The baculovirus vector comprises in sequence, a promoter; a first nucleic acid operably linked to the promoter for expressing a first protein in the mammalian or insect host cells; a chimera IRES sequence comprising a portion of an enterovirus (EV) IRES sequence at least 90% identical to SEQ ID NO: 1, and a portion of a *Rhopalosiphum padi* virus (RhPV) IRES sequence at least 90% identical to SEQ ID NO: 2; and a second nucleic acid operably linked to the chimera IRES sequence for expressing a second protein in the mammalian or insect host cells Suitable promoter for use in the baculovirus vector of the present disclosure is a cytomegalovirus (CMV) promoter, a CAG promoter composed of chicken β-actin promoter and CMV enhancer, and etc. In one example, the promoter is a CMV promoter.

The term "operably linked" refers to nucleotide sequences which are linked in the proper reading frame, whether to encode a mRNA transcript of a desired gene product or for a desired regulatory control. Operably linked can also mean that both the first and second nucleic acids are encoded by the same transcription unit. Translation of both such proteins can be regulated by various modes, including cap-dependent translation of the first open-reading-frame (ORF) located furthermost 5' on the transcription unit. Translation of the second ORF located downstream of the first ORF can be regulated by an IRES. Alternatively, both the first and second genes can be encoded by one ORF, yielding one contiguous polypeptide with both biological activities.

Proteins that may be expressed in mammalian or insect host cells using the baculoviral vectors of the present disclosure include at least, therapeutic proteins, reporter proteins or a combination thereof. Examples for the therapeutic protein include, but are not limited to, albumin, globulins (e.g., α-globuin), monoclonal antibodies, interferons, insulin, epidermal growth factor (EGF), erythropoietin, blood factors, and blood clotting factors. Proteins suitable for use as reporter proteins in this invention include, but are not limited to, easily assayed enzymes such as β-galactosidase (β-gal), luciferase (Luc) such as fire fly luciferase, *Renilla reniformis* luciferase and *Renilla muelleri* luciferase, β-glucuronidase (β-glucuronidase, GUS), chloramphenicol acetyl transferase (CAT), fluorescent proteins such as green fluorescence proteins (GFPs), enhanced green fluorescence proteins (EGFPs), coral red fluorescence proteins (DsREDs), blue fluorescence proteins (BFPs), enhanced yellow fluorescent proteins (EYFPs), *Anemonia majano* fluorescent proteins (amFPs), *Zoanthus* fluorescent proteins (zFPs), *Discosoma* fluorescent proteins (dsFPs), *Clavularia* fluorescent proteins (cFPs), and secreted embryonic alkaline phosphatase such as secreted human placental alkaline phosphatase (SEAP); proteins for which immunoassays are readily available such as hormones and cytokines; proteins which confer a selective growth advantage on cells such as adenosine deaminase, aminoglycoside phosphotransferase (the product of the neo gene), dihydrofolate reductase, hygromycin-B-phosphotransferase, thymidine kinase (when used with HAT medium i.e., a medium containing hypoxanthine, aminopterin and thymidine), xanthine-guanine phosphoribosyltransferase (XGPRT), proteins which confer a growth disadvantage on cells, for example enzymes that convert non-toxic substrates to toxic products such as thymidine kinase (when used with medium containing bromodeoxyuridine) and orotidine-5'-phosphate decarboxylase (when used with 5-fluoroorotic acid); and proteins which are toxic such as ricin, cholera toxin, botulism toxin, scorpion neurotoxin or diphtheria toxin. Methods of measuring protein levels are also well known in the art. Preferably, proteins that are expressed using the baculoviral vector of the present disclosure include one of interest introduced into the host cells and one of marker protein, which is used as an index for isolation or introduction into the host cells. In one example, the first and second proteins are respectively DsRed and EGFP.

According to one preferred embodiment of the present disclosure, the portion of EV 71 IRES sequence or a truncated EV 71 IRES sequence having SEQ ID NO: 1 may act as an enhancer of the portion of RhPV IRES sequence or a truncated RhPV IRES sequence having SEQ ID NO: 2, and is effective in enhancing the downstream protein translation activity for at least 40%, such as 40, 45, 50, 55, 60 or 65%. In one example, the translation activity for the reporter gene downstream of the RP110 segment or SEQ ID NO: 2 increases from 60% to 105% due to the presence of the truncated EV 71 IRES sequence or SEQ ID NO: 1 located before the RP110 segment.

To provide those skilled in the art the tools to use the present disclosure, the nucleic acids and host cells of this invention may be assembled to kits. The components included in the kits are viral vector, enzymatic agents for making recombinant viral constructs, cells for amplification of the viruses, and reagents for transfection and transduction into the host cells, as well as description in a form of pamphlet, tape, CD, VCD or DVD on how to use the kits.

It must be noted that as used herein and in the appended claims, the singular forms "a", "an", and "the" include plural referents unless the context clearly dictates otherwise.

The following examples are provided to illustrate the present invention without, however, limiting the same thereto.

EXAMPLES

The chimera IRES sequence, the improved baculovirus vector, and method of expressing genes using the improved baculovirus vector of the present disclosure will be illustrated in further detail with reference to several examples below, which are not intended to limit the scope of the present disclosure.

Example 1

Characterization of RhPV IRES Element 1.1 Construction of pCMV-DRhir290E, pCMV-DRhir291E, pCMV-DRhir309E, pCMV-DRhir411E and pCMV-DRhir423E It is reported that RhPV IRES contains 6 TAAG motifs within its DNA sequence that may contribute to its cryptic promoter activity within insect cells (Wu et al., Acta Pharmacol Sin 2008 29(8):965-974). To evaluate the contribution of each TAAG motif of RhPV IRES on its cryptic promoter activity within insect cells, recombinant baculovirus plasmids were constructed by inserting therein various truncated RhPV IRES elements as illustrated in FIG. 1.

In FIG. 1, the 6 TAAG motifs were respectively named L1 to L6. 5 truncated RhPV IRES elements were produced by deleting the TAAG motif sequences and thereby generating truncated RhPV IRES polynucleotide sequences 1-290, 291-579, 309-418, 411-579 and 423-579, respectively. These truncated RhPV IRES elements were respectively named Rhir290, Rhir291, Rhir309, Rhir411 and Rhir423. As illustrated in FIG. 1, Rhir290, Rhir291, Rhir309, Rhir411 and Rhir423 respectively contain therein TAAG motifs correspond to L1 to L2, L3 to L6, L3 to L4, L5 to L6, and L6.

In this example, pCMV-DRhirE (Wu et al., Biochem. and Biophys. Res. Commu. 2005 335:616-623) was used as a template and digested with EcoRI and BamHI to remove the full length RhPV IRES fragment therein. The above described truncated RhPV IRES sequences (i.e., Rhir290, Rhir291, Rhir309, Rhir411 and Rhir423) were amplified, and pCR2.1 were used for TA cloning, and the resultant plasmids were named pCR2.1/Rhir290, pCR2.1/Rhir291, pCR2.1/Rhir309, pCR2.1/Rhir411 and pCR2.1/Rhir423, respectively. The thus obtained plasmids were digested with EcoRI and BamHI to remove Rhir290, Rhir291, Rhir309, Rhir411 and Rhir423 fragments. The removed Rhir290, Rhir291, Rhir309, Rhir411 and Rhir423 fragments were then ligated to the EcoRI and BamHI site of the pCMV-DRhirE plasmid, and the resulting plasmids were respectively named pCMV-DRhir290E, pCMV-DRhir291E, pCMV-DRhir309E, pCMV-DRhir411E and pCMV-DRhir423E, as illustrated in FIG. 1.

1.2 Production of Recombinant Baculoviurs Vectors

*S. furgiperda* IPBL-sf21 insect cell line (herein after "Sf21 cells") were cultured in TNM-FH medium containing 8-10% heat-inactivated fetal bovine serum (FBS) until a confluent cell monolayer was obtained. The plasmids of example 1.1 were transfected into Sf21 cells ($2\times10^5$ cellsper well in a 24-well plate) together with the linearized viral DNA Bac-N-Blue (0.25 μg, Invitrogen Corp, Carlsbad, Calif., USA) by use of 1 ml of CELLFECTIN™ Transfection Reagent. The transfected cells were cultured in TNM-FH medium for 3 to 4 days. If DNA homologous recombination occurred among Bac-N-Blue baculovirus DNA and the plasmids of example 1.1, then new recombinant baculovirus vectors are formed, and the newly formed recombinant baculovirus vectors could be selected by end-point dilution method with the aid of the green fluorescence emitted from the co-expressed EGFP. The selected recombinant baculovirus vectors were thus named vCMV-DRhirE, vCMV-DRhir290E, vCMV-DRhir291E, vCMV-DRhir309E, vCMV-DRhir411E, and vCMV-DRhir423E, respectively.

1.3 Characterization of the Promoter Activity of the RhPV IRES Elements in Insect Cells Sf21 cells ($2 \times 10^5$ cellsper well in a 24-well plate) were transfected with the recombinant baculovirus vectors of example 1.2, and fluorescence pattern of the transfected cells were observed using fluorescence spectrophotometer (Varian) with excitation and emission wavelength set at 488 nm and 507 nm, respectively.

Figure 2:
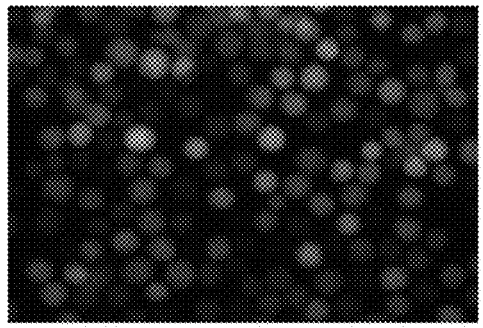
FIG. 2 are fluorescent photographs of Sf21 cells taken on day 4 after being transfected with recombinant baculovirus vectors of example 1.2, including (A) pCMV-DRhirE, (B) pCMV-DRhir290E, (C) pCMV-DRhir291E, (D) pCMV-DRhir309E, (E) pCMV-DRhir411E, and (F) pCMV-DRhir423E.
Figure 2:
Figure 2:
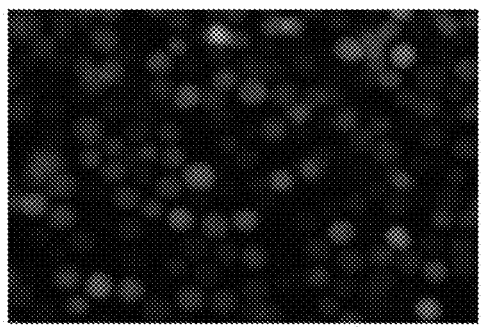
Figure 2:
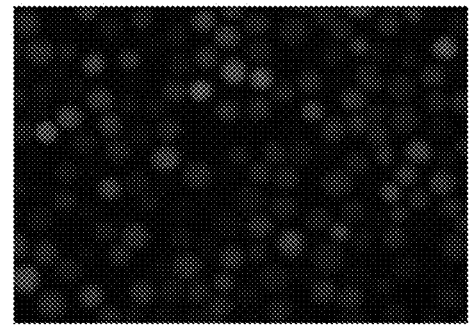
Figure 2:
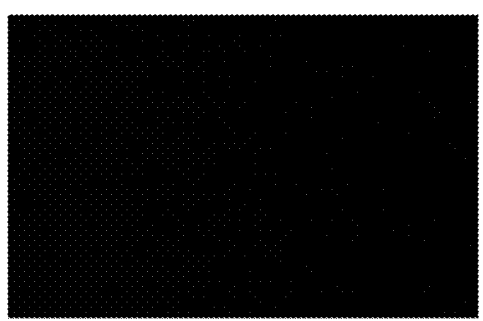
Figure 2:
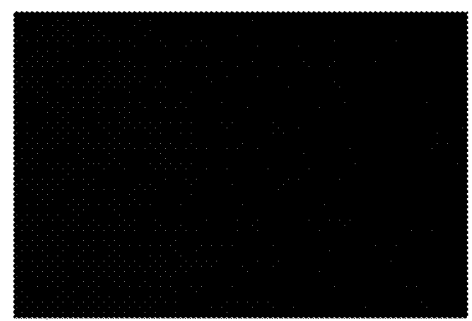
Figure 3:
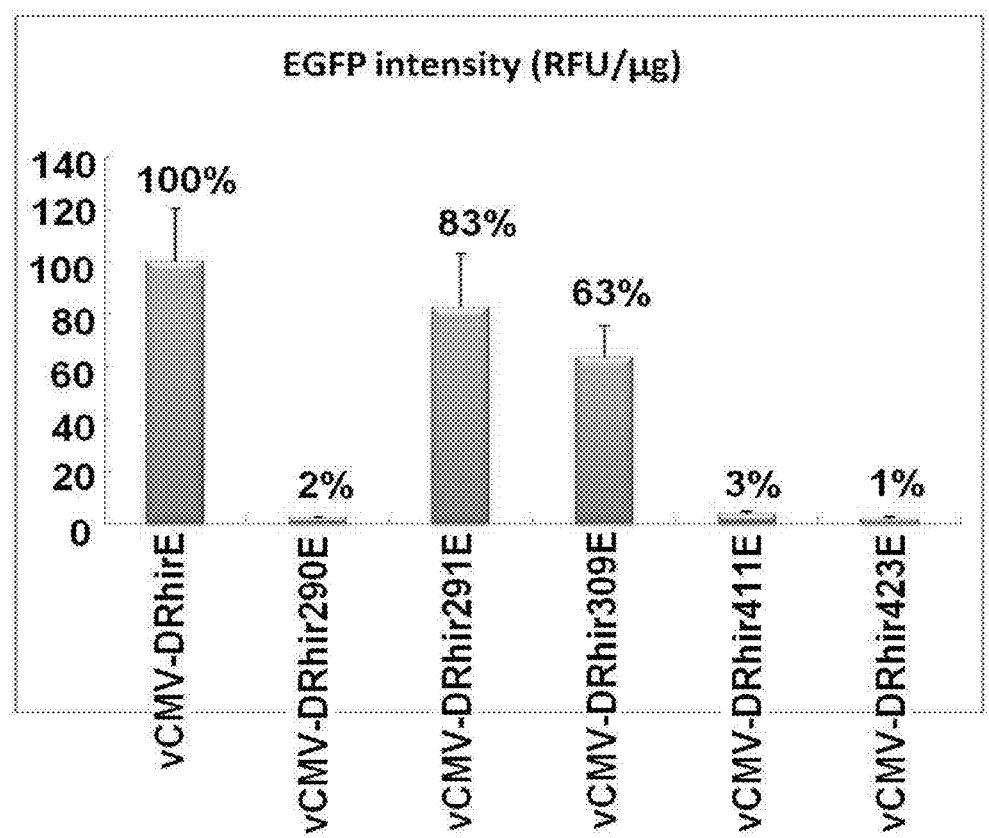
FIG. 3 is a bar diagram illustrating the quantification result of EGFP expression on day 4 in Sf21 cells infected with the recombinant baculovirus vectors of example 1.2.

Results are illustrated in FIGS. 2 and 3.

FIG. 2 illustrates the green fluorescence pattern in Sf21 cells respectively transfected with the recombinant baculovirus vectors of (A) vCMV-DRhirE, (B) vCMV-DRhir290E, (C) vCMV-DRhir291E, (D) vCMV-DRhir309E, (E) vCMV-DRhir411E, and (F) vCMV-DRhir423E. By day 4, green fluorescence was evident from Sf21 cells infected with vCMV-DRhirE, vCMV-DRhir291E or vCMV-DRhir309E. In view of this finding, it is reasonable to conclude that among the 6 TAAG motifs within the RhPV IRES sequence that were respectively named L1 to L6, each of L1, L2, L5 and L6 has minimum contribution in terms of the promoter activity of RhPV IRES sequence, whereas the tandem repeated TAAG motifs (i.e., L3 and L4) are a must for such activity.

To verify the observation made in FIG. 2, the above transfected Sf21 cells were respectively lysed with a lysing buffer which comprises 100 mM potassium phosphate (pH7.8), 1 mM EDTA, 10% Triton X-100, and 7 mM β-mercaptoethanol; and the expressed EGFP were collected and quantified. Results are illustrated in FIG. 3.

FIG. 3 is a bar diagram illustrating the quantification result of EGFP expression on day 4 in Sf21 cells infected with the recombinant baculovirus vectors of example 1.2. Quantification of the expressed EGFP confirms the finding made in FIG. 2, and the two tandem repeated TAAG motifs (i.e., L3 and L4) confer over 60% promoter activity of RhPV IRES element. This truncated RhPV IRES element, which corresponds to nucleotide sequence from position 309 to 418 of RhPV IRES, is thus termed RP110 promoter in the present disclosure, in which RP stands for *Rhopalosiphum padi*, and 110 stands for the size of this promoter (i.e., 110 nucleotides in length).

1.4 Characterization of the Translation Activity of RhPV IRES Elements in Mammalian Cells Chinese hamster ovarian (CHO) cell lines were cultured in Dulvecco's Modified Eagle's Medium (DMEM) supplemented with 10% heat-inactivated fetal bovine serum (FBS) and maintained at 37° C. in an environment containing 5% $CO_2$ until a confluent cell monolayer was obtained. Then, the cultured CHO cells ($9 \times 10^4$ cells per well in a 24-well plate) were transfected with the recombinant baculovirus plasmids of example 1.1 with the aid of lipofection reagent and fluorescence pattern of the transfected cells at day 2 were observed using fluorescence spectrophotometer (Varian). Results are illustrated in FIG. 4.

Figure 4:
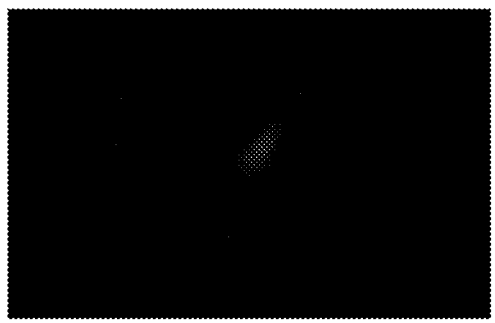
FIG. 4 are fluorescent photographs illustrate the red and green fluorescence patterns in CHO cells respectively transfected with the recombinant baculovirus plasmids of example 1.1, including (A) pCMV-DRhirE, (B) pCMV-DRhir290E, (C) pCMV-DRhir291E, (D) pCMV-DRhir309E, (E) pCMV-DRhir411E, and (F) pCMV-DRhir423E.
Figure 4:
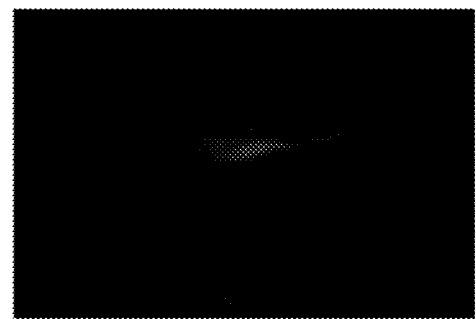
Figure 4:
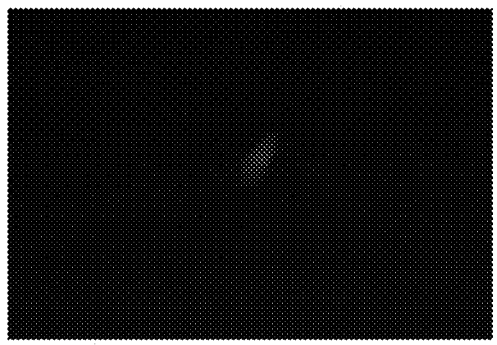
Figure 4:
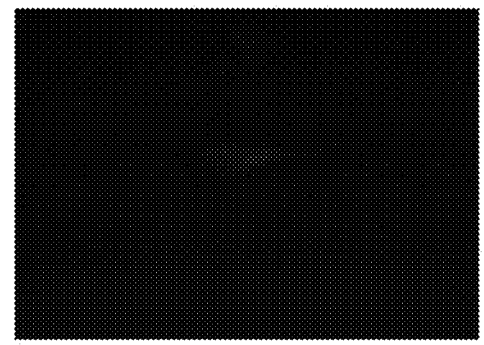
Figure 4:
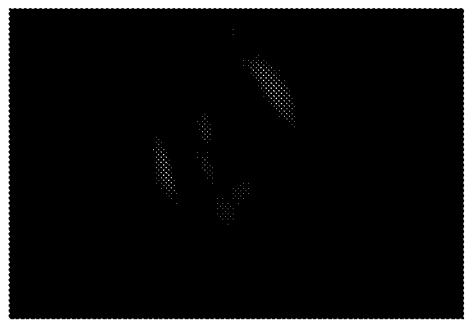
Figure 4:
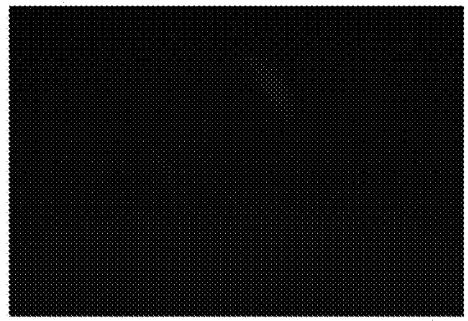
Figure 4:
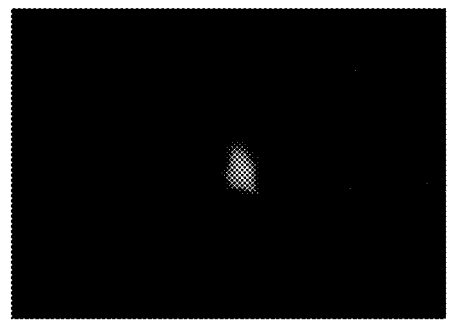
Figure 4:
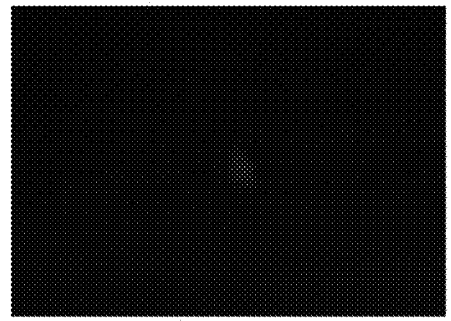
Figure 4:
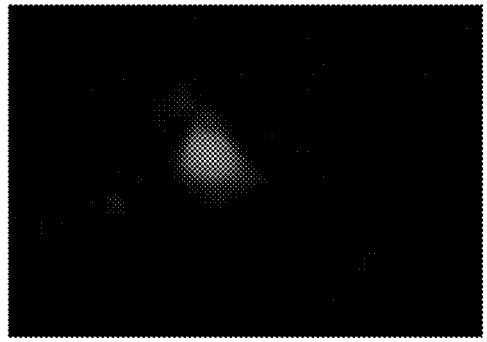
Figure 4:
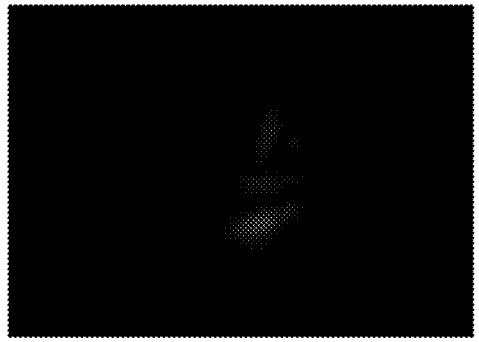
Figure 4:
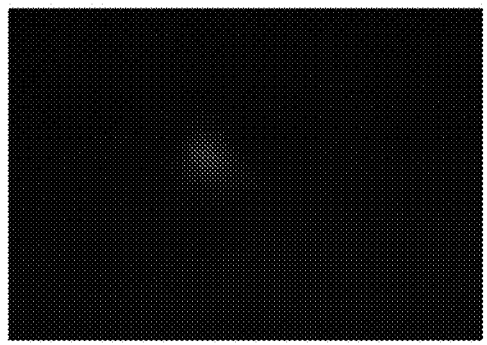
Figure 4:

FIG. 4 illustrates the red and green fluorescence patterns in CHO cells respectively transfected with the recombinant baculovirus plasmids of (A) pCMV-DRhirE, (B) pCMV-DRhir290E, (C) pCMV-DRhir291E, (D) pCMV-DRhir309E, (E) pCMV-DRhir411E, and (F) pCMV-DRhir423E. Green and red fluorescence remained evident from CHO cells transfected with either plasmid containing a truncated RhPV IRES element of example 1.1, indicating that the IRES activity of the RhPV IRES element in mammalian cells was not affected by the deletion of TAAG motifs. In other words, there is no specific sequence within the RhPV IRES element that is determinable on its IRES activity in mammalian cells.

Example 2

Characterization of RP110

2.1 Construction of Recombinant Vectors Containing RP110 Having Point Mutations Therein To verify which TAAG motif is necessary for the identified promoter activity of RP110, point mutations were introduced into respective TAAG motif termed L3 and L4. Specifically, 3 mutants were produced by deleting the entire TAAG motif and by mutating thymidine nucleotide (T) of L3 and L4 into adenine (A), and thereby generating Rhir309 TAAGΔ, Rhir309 T328A, and Rhir309T332A mutants.

Figure 5:
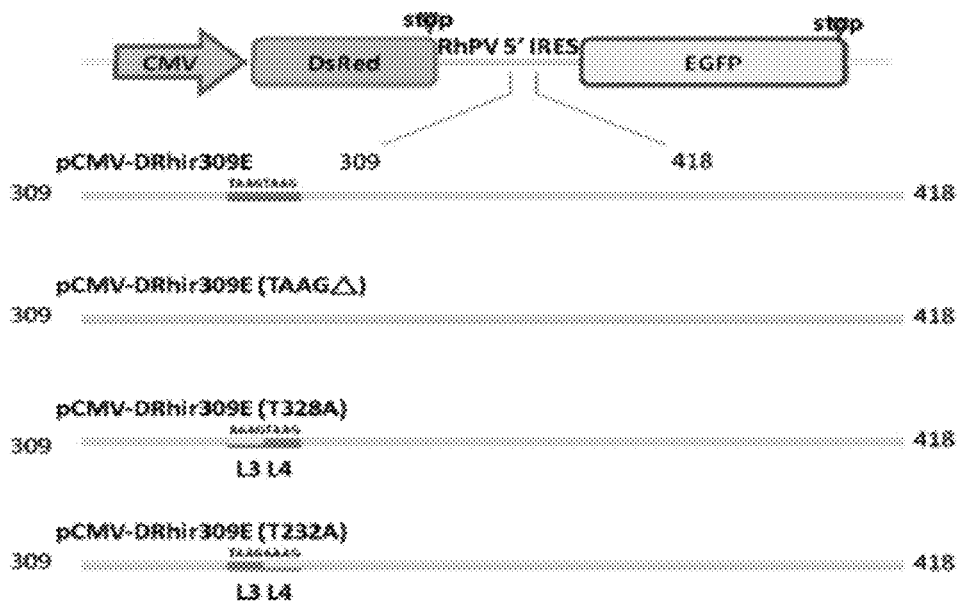
FIG. 5 is a schematic diagram illustrating the construction of recombinant baculovirus plasmids in accordance with one embodiment of this invention.

In operation, the plasmids containing the mutated sequences described above were constructed (i.e., pCMV-DRhir309E (TAAGTAAGΔ), pCMV-DRhir309E (T328A) and pCMV-DRhir309E (T332A), see FIG. 5) and linearized with viral DNA to form recombinant vectors in accordance with similar steps described in examples 1.1 and 1.2. The thus produced recombinant vectors were named vCMV-DRhir309E (TAAGΔ), vCMV-DRhir309E (T328A) and vCMV-DRhir309E (T332A), respectively.

2.2 Characterization of the Promoter Activity of RP110 in Insect Cells

Sf21 cells ($2 \times 10^5$ cellsper well in a 24-well plate) were transfected with the recombinant baculovirus vectors of example 2.1, and fluorescence pattern of the transfected cells were observed in accordance with similar steps as described in example 1.3. Results are illustrated in FIG. 6.

FIG. 6 illustrates the green fluorescence pattern in Sf21 cells respectively transfected with the recombinant baculovirus vectors (A) vCMV-DRhir309E, (B) vCMV-DRhir309E (TAAGΔ), (C) vCMV-DRhir309E (T328A), and (D) vCMV-DRhir309E (T332A). By day 4, green fluorescence was evident from all Sf21 cells infected with the recombinant vectors. However, fluorescence intensity was much higher in cells transfected with vCMV-DRhir309E (T332A) than those with vCMV-DRhir309E (T328A). Hence, it is reasonable to conclude that TAAG motif is indeed the site for transcription initiated by the late promoter, therefore, deletion of the late promoter would completely abolish the expression of the downstream reporter gene, that is, the expression of EGFP.

To quantify the expressed EGFP, transfected cells were lysed and the expressed EGFP were collected and quantified in accordance with steps described in example 1.3. Results were illustrated in FIG. 7.

Figure 7:
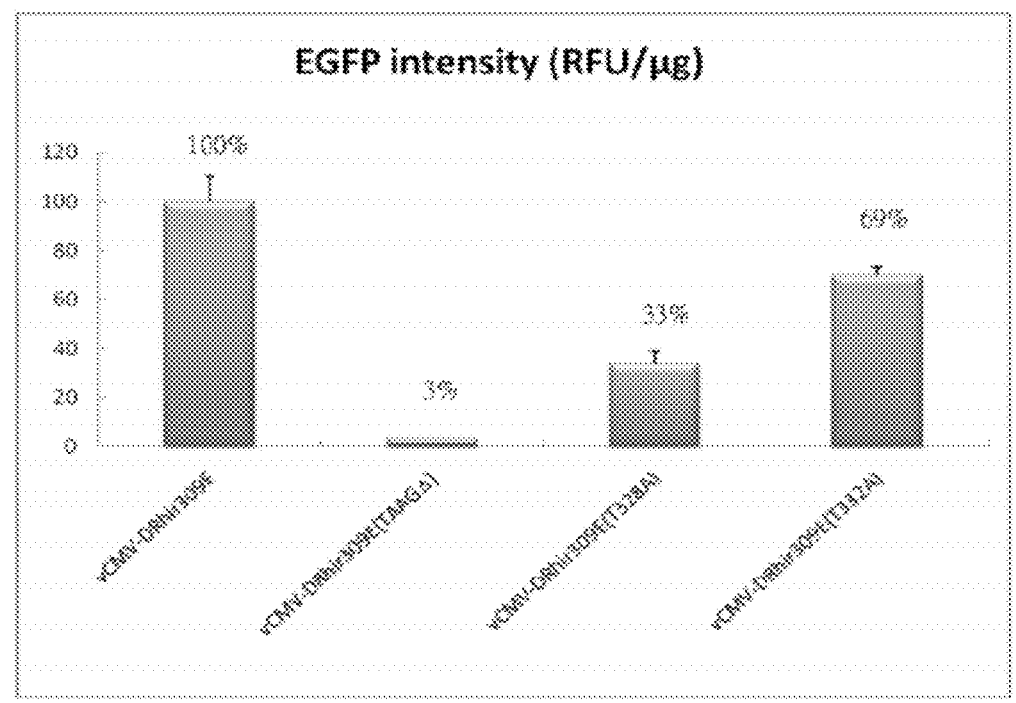
FIG. 7 is a bar diagram illustrating the quantification result of EGFP expression on day 4 in Sf21 cells infected with the recombinant baculovirus vectors of Example 2.1.

FIG. 7 is a bar diagram illustrating the quantification result of EGFP expression on day 4 in Sf21 cells infected with the recombinant baculovirus vectors of example 2.1. Quantification of the expressed EGFP confirms the finding made in FIG. 6, and the TAAG motif in L3 weights more than the TAAG motif in L4 in terms of the promoter activity of RhPV IRES Elements.

2.3 Characterization of the IRES Activity of RP110 in Mammalian Cells

Figure 8:
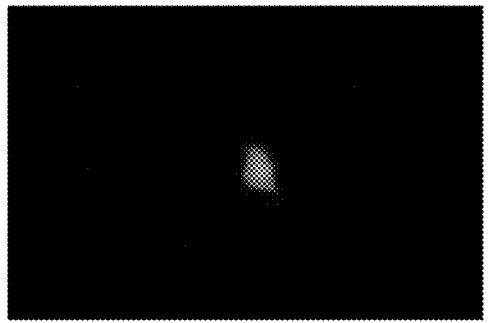
FIG. 8 are fluorescent photographs illustrate the red and green fluorescence patterns in CHO cells respectively transfected with the recombinant baculovirus plasmids of example 1.1, including (A) vCMV-DRhir309E, (B) vCMV-DRhir309E (TAAGΔ), (C) vCMV-DRhir309E (T328A), and (D) vCMV-DRhir309E (T332A)
Figure 8:
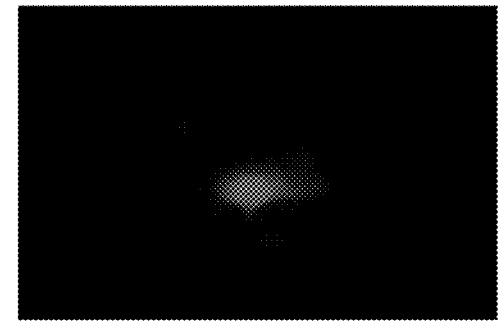
Figure 8:
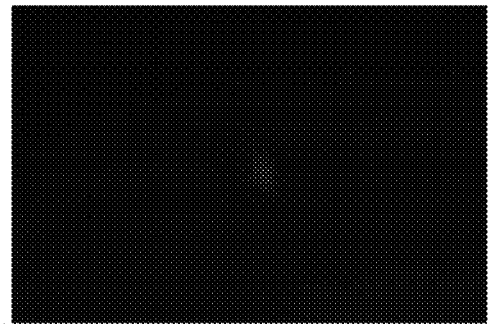
Figure 8:
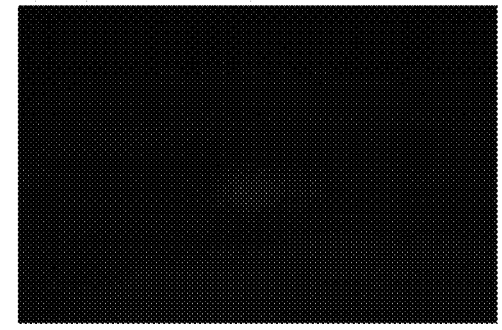
Figure 8:
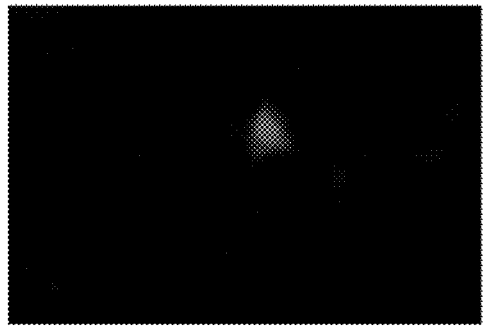
Figure 8:
Figure 8:
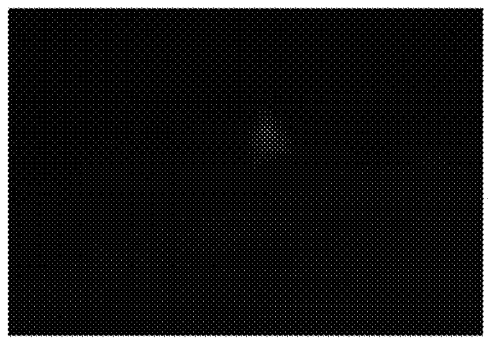
Figure 8:
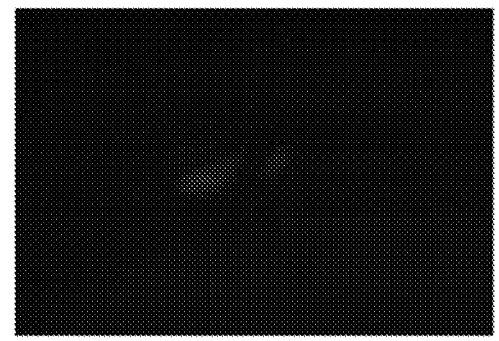

The IRES activity of RP110 in mammalian cells was studied in CHO cells in accordance with steps described in example 1.5. Fluorescent patterns of the transfected CHO cells were respectively observed on day 2 and results are provided in FIG. 8. Red and green fluorescence were both evident in all transfected cells indicating that IRES activity of the RP110 is not slightly affected with or without the deletion and/or mutation in L3 and L4.

Example 3

Construction of Improved Baculovirus Vectors Comprising RP 110 and a Portion of EV71 IRES Element 3.1 Construction of Artificial Baculovirus Vectors Comprising RP 110 and a Portion of EV71 IRES Element In view of the finding presented in examples 1 and 2, the inventors confirm that over 60% of the cryptic promoter activity of RhPV IRES element lies within the polynucleotide sequence starting from position 309 to 418 (i.e., RP 110); and the IRES activity of said RP 110 sequence remains relatively unchanged in mammalian host cells. Artificial baculorvirus vectors that may be effective in both insect and mammalian host cells for gene transfer were then constructed using the identified RP110 promoter sequence and the previously identified EV71 IRES truncate as an enhancer.

Figure 9:
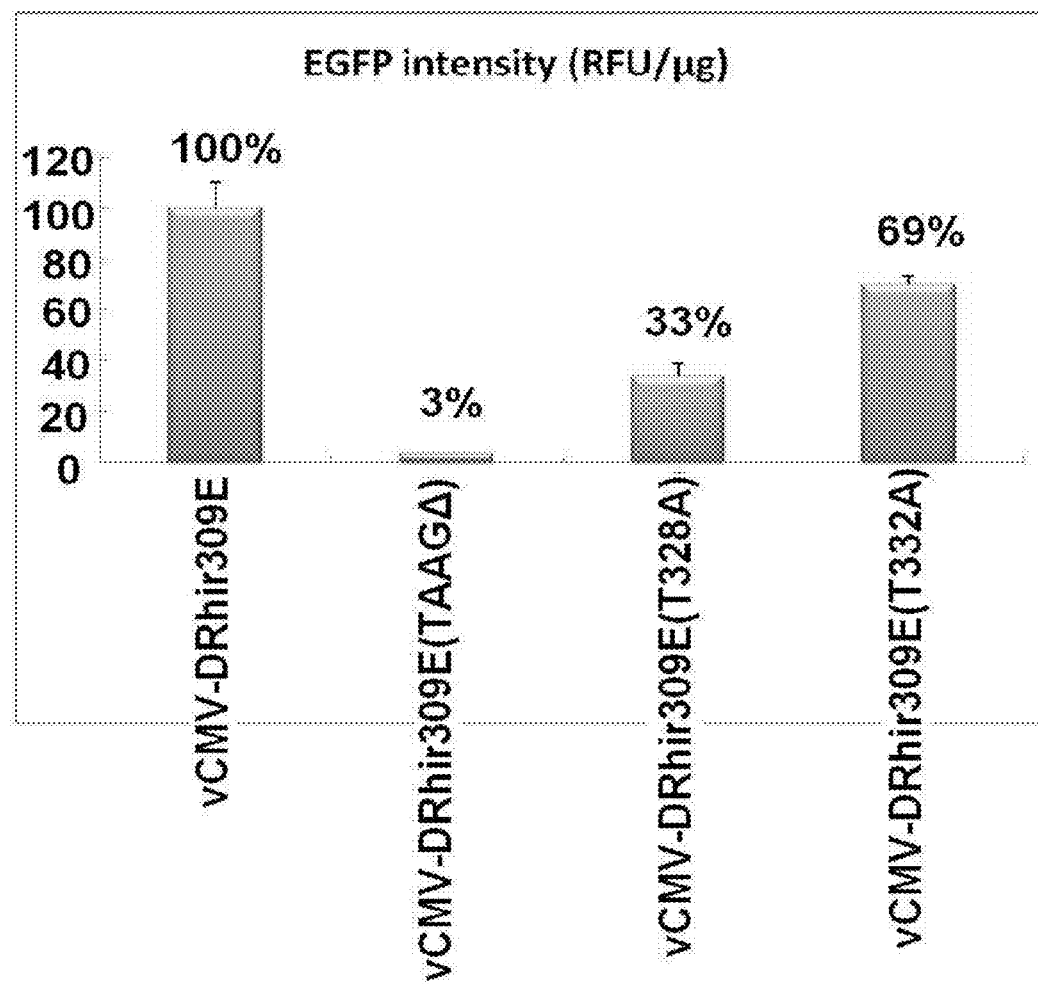
FIG. 9 is a schematic diagram depicting the truncated EV71 IRES sequences produced in according with one embodiment of this invention.

Briefly, various truncated enterovirus 71 (EV71) IRES elements were generated by making deletions from its 5'- or 3'-end. FIG. 9 is a schematic diagram depicting the truncated EV71 IRES sequences thus produced, which are termed 5'Δ100, 5'Δ145, 5'Δ200, 3'Δ100, 3'Δ145, 3'Δ200, and 3'Δ245, respectively. Further studies confirm that the 3'Δ100 truncate does not affect the IRES activity of EV71 IRES element in mammalian host cells including CHO, cos-1 and N2A cells (data not shown), hence, this particular 3'Δ100 truncate of EV71 IRES element was selected to be an enhancer for constructing the artificial baculovirus vectors of this example.

Figure 10:
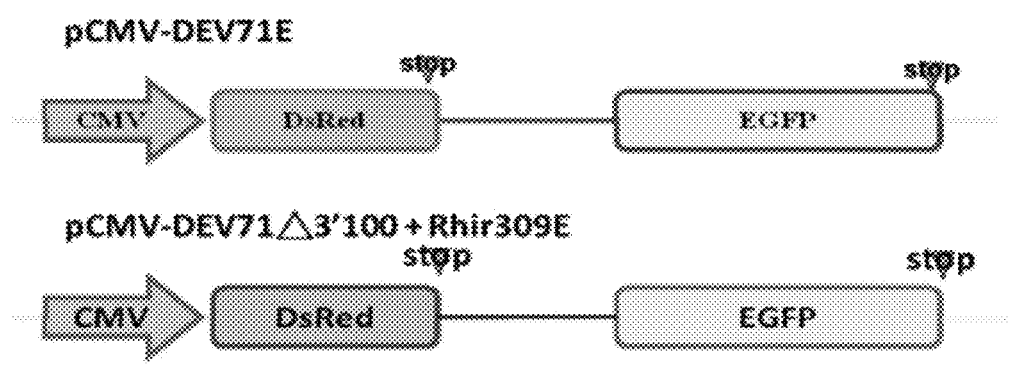
FIG. 10 is a schematic diagram depicting the EV 71 3'Δ100 Rhir 309 expression cassette in accordance with one embodiment of this invention.

Briefly, pCMV-DEV71E was used to synthesize primers EV71 IRESΔ3' 100-EcoR I-F and EV71 IRESΔ3' 100-Mun I-R. These two primers were then used to amplify EV71 IRESΔ3' 100 fragments from pCMV-DEV71E. The thus amplified EV71 IRESΔ3' 100 fragments and pCR2.1 were used for TA cloning and thereby generating pCR2.1/EV71 IRESΔ3' 100 constructs. The plasmids were then digested with EcoR I and Mun I, the cut out EV71 IRESΔ3' 100 was then ligated with EcoR I treated pCMV-DRhir309E and thereby generating the desired pCMV-DEV71Δ3'100 expression cassette, which comprises 3'Δ100 truncate of EV71 IRES element and RP110 as depicted in FIG. 10.

The thus produced pCMV-DEV71Δ3'100 expression cassette was linearized with viral DNA to form the desired artificial vector in accordance with similar steps described in examples 1.1 and 1.2. The thus produced artificial vector was named vCMV-D EV71Δ3'100 Rhir 309E.

3.2 Characterization of the Promoter Activity of vCMV-D EV71Δ3'100 Rhir 309E in Insect Cells Sf21 cells (2×10⁵ cellsper well in a 24-well plate) were transfected with the recombinant baculovirus vectors including vCMV-DRhirE, vCMV-DRhir309E, vCMV-DEV71E and vCMV-D EV71Δ3'100 Rhir 309E; in which vCMV-DRhirE and vCMV-DRhir309E were used as positive controls, and vCMV-DEV71E was used as a negative control. Fluorescence pattern of the transfected cells were observed in accordance with similar step described in example 1.3. Results are illustrated in FIG. 11.

FIG. 11 illustrates the green fluorescence pattern in Sf21 cells respectively transfected with the recombinant baculovirus vectors, including (A) vCMV-DRhirE, (B) vCMV-DRhir309E, (C) vCMV-DEV71E and (D) vCMV-D EV71Δ3'100 Rhir 309E. By day 4, green fluorescence was evident from Sf21 cells infected with vCMV-DRhirE, vCMV-DRhir309E and vCMV-D EV71Δ3'100 Rhir 309E except those infected with vCMV-DEV71E. Hence, it is reasonable to conclude that EV71 IRES is not effective in insect cells in terms of its IRES activity.

To quantify the expressed EGFP, transfected cells were lysed and the expressed EGFP were collected and quantified in accordance with steps described in example 1.3. Results were illustrated in FIG. 12.

FIG. 12 is a bar diagram illustrating the quantification result of EGFP expression on day 4 in Sf21 cells infected with the recombinant baculovirus vectors including (A) vCMV-DRhirE, (B) vCMV-DRhir309E, (C) vCMV-DEV71E and (D) vCMV-D EV71Δ3'100 Rhir 309E. Quantification of the expressed EGFP confirms the finding of FIG. 11. Fluorescence intensity in cells infected with CMV-DRhir309E, vCMV-DEV71E and vCMV-D EV71Δ3'100 Rhir 309E were 60%, 2% and 105%, respectively, compared with the control (i.e., cells infected with vCMV-DRhirE). The results confirm that the truncated EV71 IRES element, specifically, 3'Δ100 truncate of EV71 IRES element, may enhance the promoter activity of RP 110 by at least 45%, form 60% to 105%.

Figure 13:
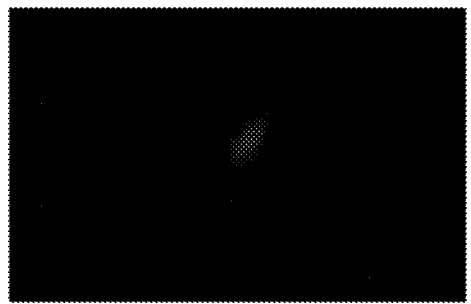
FIG. 13 are fluorescent photographs illustrate the red and green fluorescence patterns in CHO cells respectively transfected with the recombinant baculovirus vectors, including (A) vCMV-DRhir309E, (B) vCMV-DRhir309E, (C) vCMV-DEV71E, and (D) vCMV-DEV71 (3'100) Rhir309E.
Figure 13:
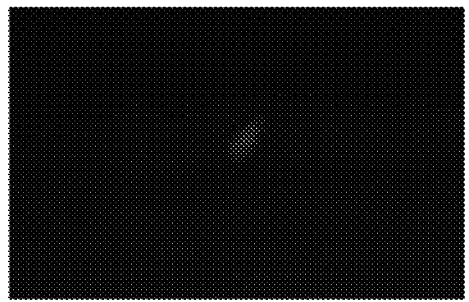
Figure 13:
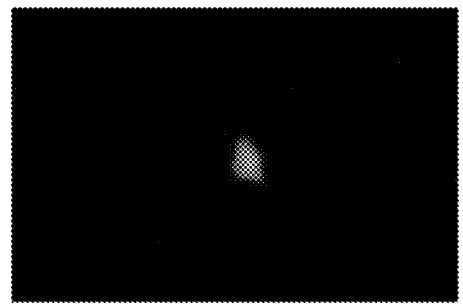
Figure 13:
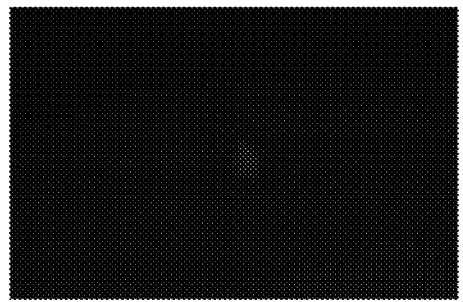

3.3 Characterization of the IRES Activity of vCMV-D EV71A3'100 Rhir 309E in Mammalian Cells The IRES activity of vCMV-D EV71Δ3'100 Rhir 309E in mammalian cells was studied in CHO cells in accordance with similar steps described in example 1.5. Fluorescent patterns of the transfected CHO cells were respectively observed on day 2 and results are provided in FIG. 13. Red and green fluorescence were both evident in all transfected cells indicating that IRES activity of RP110 is not affected by the inclusion of the 3' truncate of EV71 IRES.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A chimera internal ribosomal entry site (IRES) sequence for use in mammalian or insect host cells comprising the nucleotide sequence of SEQ ID NO: 1; and the nucleotide sequence of SEQ ID NO: 2.

2. A baculovirus vector for use in mammalian or insect host cells comprising:
a promoter;
a first nucleic acid operably linked to the promoter for expressing a first protein in the mammalian or insect host cells;
a chimera internal ribosomal entry site (IRES) sequence comprising the nucleotide sequence of SEQ ID NO: 1 and the nucleotide sequence of SEQ ID NO: 2; and
a second nucleic acid operable linked to the chimera IRES for expressing a second protein in the mammalian or insect host cells.

3. The baculovirus vector of claim 2, wherein the promoter is a cytomegalovirus (CMV) promoter or a CAG promoter composed of chicken β-actin promoter and CMV enhancer.

4. The baculovirus vector of claim 2, wherein the sequence of SEQ ID NO: 2 has a promoter activity and is effective to express downstream nucleic acid sequence in an insect host cell.

5. The baculovirus vector of claim 4, wherein the insect host cell is a *S. frugiperda* IPBL-Sf21 insect cell.

* * * * *